Sept. 30, 1969 P. ECKE Plant Pat. 2,926
POINSETTIA PLANT
Filed Feb. 27, 1968
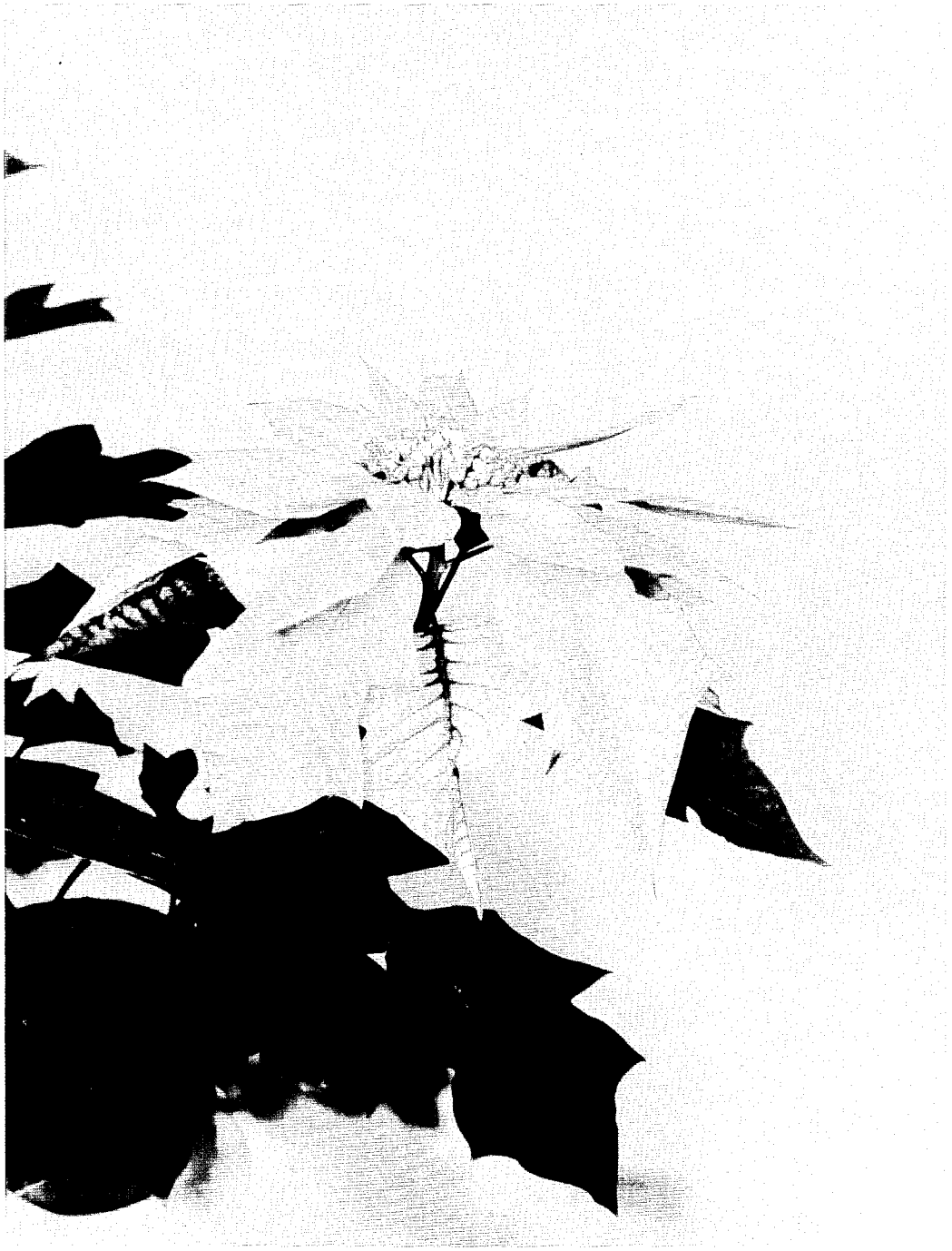
Inventor.
Paul Ecke
By: Robb & Robb
Attorneys.

United States Patent Office

Plant Pat. 2,926
Patented Sept. 30, 1969

2,926
POINSETTIA PLANT

Paul Ecke, Encinitas, Calif., assignor to Paul Ecke, Inc., Encinitas, Calif., a corporation of California Filed Feb. 27, 1968, Ser. No. 708,731
Int. Cl. A01h 5/12
U.S. Cl. Plt.—86 1 Claim The present invention relates to a new and distinct variety of poinsettia plant botanically known as *Euphorbia pulcherrima*) which was originated by me by crossing an unnamed and unpatented red poinsettia seedling with another unnamed and unpatented red poinsettia seedling, the former being the seed parent, and the latter being the pollen parent.

The primary objectives of this breeding were to produce a new and improved early blooming poinsettia variety having an unusual apricot shade of pink color, a bract conformation wherein the smaller inner bracts are horizontal and the larger outer bracts twist, giving an overall umbrella appearance, and having bracts and leaves which are long lasting. These objectives were fully achieved, along with other desirable features, as evidenced by the following unique combination of characteristics which are outstanding in the new variety and which distinguish it from its parents, as well as from all other varieties of which I as aware:

(1) A very vigorous, tough and durable plant habit;
(2) Thin but stiff stems which do not require staking;
(3) A very vigorous and extensive root system;
(4) Retention of the bracts, foliage and inflorescence for an unusually long period of time after reaching maturity;
(5) A normally earlier blooming habit, usually 9 weeks after the start of short days, but having the ability to be satisfactorily brought into bloom and full maturity in every month of the year through the exercise of proper greenhouse cultural techniques;
(6) A distinctive and attractive appearance of the bracts, with the small inner bracts being horizontal and the larger outer bracts twisting and giving an overall umbrella appearance;
(7) A distinctive, attractive and unusual general color tonality of the bracts corresponding to Delft Rose;
(8) A medium tall growing habit when grown naturally;
(9) The ability to pinch well;
(10) A suitability for the production of multiple bloom plants, and
(11) Excellent keeping qualities and consequent suitability for home decoration.

Asexual reproduction of my new variety by vegetative cuttings propagated under mist at Encinitas, Calif., shows that the foregoing characteristics and distinctions come true to form and are established and transmitted through succeeding propagations.

The accompanying drawing shows a typical specimen plant of my new variety as depicted in color as nearly true as it is reasonably possible to make the same in a color illustration of this character.

The following is a detailed description of my new poinsettia variety, with color terminology in accordance with Wilson's Horticultural Colour Chart, except where general color terms of ordinary dictionary significance are obvious, as based on specimens grown at Encinitas, Calif., under regular commercial practices:

Parentage: Seedling.
*Seed parent.*—An unnamed red seedling.
*Pollen parent.*—An unnamed red seedling.

Propagation: Holds its distinguishing characteristics through succeeding propagations by vegetative cuttings.

Form: Medium tall; upright.

Habit of growth: Vigorous; medium upright; thin, stiff stems which do not require staking.

Rooting habit: Very fast (from 12 to 15 days under mist); vigorous; extensive; uniform.

Blooming habit: Approximately 9 weeks after start of short days.

Blooming season: Can be satisfactorily brought into bloom in every month of the year by appropriate greenhouse culture practices.

Foliage: Alternate; borne horizontally on stems; persistent; normal quantity.
*Size.*—Medium (from about 3 inches to 7 inches long); width from about 2½ inches to 4 inches.
*Shape.*—Serrated; long pointed.
*Texture.*—Upper side—semi-glossy; ordinary recessed veins. Under side—dull; ordinary protruding veins.
*Margin.*—Well defined.
*Color.*—New foliage: upper side—near Scheele's Green, Plate 860, page 175; lower side—near Scheele's Green, Plate 860/1, page 175. Old foliage: upper side—near Spinach Green, Plate 0960/1, page 187; lower side—near Leek Green, Plate 000858/1, page 197.

Disease resistance: Resistant to rhizoctonia and pythium stem and root rot during propagation and growing period, and resistant to botrytis during blooming period, as determined by comparison with other plants grown under the same cultural conditions at Encinitas, Calif. which are infected with these diseases.

Bracts: Many (approximately 20 to 25 in number); well defined; from narrow to wide; medium length, excellent retention; new bracts form and develop as other bracts mature; very long lasting qualities; short pointed when young, but becoming medium pointed at maturity; new bracts retain their relative horizontal position and do not droop, but original older bracts have graceful, twisting, arching form comparable to an umbrella effect; retain their color exceptionally well; lower bracts quite ruffled, but upper bracts only slightly ruffled in appearance; have medium length petioles giving an overall reasonably full appearance. Color: upper side—near Delft Rose, Plate 020/2, page 108; under side—slightly lighter than Delft Rose, Plate 020/3, page 108.

Flowers:
*Borne.*—Continuously for several months; many flowers per stem in regular clusters in varying stages of development; borne on strong medium length stems; slow development, giving a compact appearance for a greater period of time; position of flowers remains relatively low without rising as it does in other commercial poinsettia varieties during early development, and does not spread out during later stages of development, thereby giving a more attractive appearance for a longer period of time.
*Quantity of bloom.*—Relatively abundant; continuous; flowers gradually drop off after maturity, but new ones continue to develop as flower stems continue to grow.
*Buds.*—From small to medium size; borne on light green stems. Color—near Lettuce Green, Plate 861/3, page 176.

Reproductive organs:
*Stamens.*—Few; from about ⅛ inch to ¼ inch long. Color—near Delft Rose, Plate 020/2, page 108.
*Pollen.*—Color—near Naples Yellow, Plate 403, page 121.

*Styles.*—Color—near Rose Opal, Plate 022, page 110.

*Ovaries.*—Color—near Lettuce Green, Plate 861/2, page 176.

*Nectar cups.*—Color—near Naples Yellow, Plate 403, page 121.

General observations: As compared with its unnamed seed parent, the new variety principally differs from this parent in that it is pink in color, whereas this parent is red in color. As compared with its unnamed pollen parent, the new variety principally differs from this parent in that it has a shorter habit of growth and is pink in color whereas the parent is taller and is red in color.

I claim:

1. A new and distinct variety of poinsettia plant, substantially as herein shown and described, characterized particularly as to novelty by the unique combination of a very vigorous, tough and durable plant habit, thin but stiff stems which do not require staking, a very vigorous and extensive root system, retention of the bracts, foliage and inflorescences for an unusually long period of time after reaching maturity, a normally earlier blooming habit usually 9 weeks after start of short days, but having the ability to be satisfactorily brought into bloom and full maturity in every month of the year through the exercise of proper greenhouse cultural techniques, a distinctive and attractive appearance of the bracts, with the smaller inner bracts being horizontal and the larger outer bracts twisting and giving an overall umbrella appearance, a distinctive, attractive and unusual general color tonality of the bracts corresponding to Delft Rose, a medium-tall growing habit when grown naturally, the ability to pinch well, a suitability for the production of multiple bloom plants, and excellent keeping qualities and consequent suitability for home decoration.

No References Cited

ROBERT E. BAGWILL, Primary Examiner